(12) United States Patent
Tieszen

(10) Patent No.: US 6,663,260 B1
(45) Date of Patent: Dec. 16, 2003

(54) EQUIPMENT WORK LIGHT RING

(76) Inventor: Dwayne A. Tieszen, P.O. Box 428, Ponder, TX (US) 76259

( * ) Notice: Subject to any disclaimer, the term of this patent is extended or adjusted under 35 U.S.C. 154(b) by 0 days.

(21) Appl. No.: 10/200,112

(22) Filed: Jul. 23, 2002

(51) Int. Cl.$^7$ .............................................. F21V 21/00
(52) U.S. Cl. ........................ 362/249; 362/398; 362/33
(58) Field of Search ................................ 362/249, 240, 362/109, 398, 252, 800, 33, 216, 226, 227

(56) References Cited

U.S. PATENT DOCUMENTS

| | | | | |
|---|---|---|---|---|
| 4,536,732 A | * | 8/1985 | Schindl et al. | 335/285 |
| 4,729,070 A | * | 3/1988 | Chiu | 362/33 |
| 5,143,436 A | * | 9/1992 | Baylor et al. | 362/582 |
| 5,289,355 A | | 2/1994 | Cimock | 362/86 |
| 5,473,519 A | | 12/1995 | McCallops et al. | 362/120 |
| 5,525,842 A | | 6/1996 | Leininger | 290/54 |
| 5,615,941 A | | 4/1997 | Shecter | 362/109 |
| 5,735,592 A | | 4/1998 | Shu | 362/118 |
| 5,838,247 A | | 11/1998 | Bladowski | 340/815.45 |
| D403,091 S | | 12/1998 | McCalla | D26/38 |
| D406,370 S | | 3/1999 | McCalla | D26/38 |
| D406,669 S | | 3/1999 | McCalla | D26/38 |
| 5,984,493 A | | 11/1999 | Higgins et al. | 362/283 |
| 6,030,092 A | | 2/2000 | McCalla et al. | 362/120 |
| 6,033,081 A | | 3/2000 | Huang | 362/119 |
| 6,036,087 A | | 3/2000 | Hong et al. | 235/375 |
| 6,168,301 B1 | | 1/2001 | Martinez et al. | 362/500 |
| 6,260,982 B1 | | 7/2001 | Huebner | 362/147 |
| 6,280,055 B1 | * | 8/2001 | Merko | 362/235 |
| 6,318,874 B1 | | 11/2001 | Matsunaga | 362/119 |
| 6,322,226 B1 | * | 11/2001 | Dickson | 362/33 |
| 6,322,237 B1 | * | 11/2001 | Lee | 362/500 |
| 6,329,676 B1 | | 12/2001 | Takayama et al. | 257/95 |
| 6,454,437 B1 | * | 9/2002 | Kelly | 362/246 |
| 6,491,417 B1 | * | 12/2002 | Haen et al. | 362/485 |
| 6,554,452 B1 | * | 4/2003 | Bourn et al. | 362/247 |

FOREIGN PATENT DOCUMENTS

WO    WO 01/24583 A1    4/2001

* cited by examiner

Primary Examiner—Alan Cariaso
Assistant Examiner—Ali Alavi
(74) Attorney, Agent, or Firm—Richard C. Litman

(57) ABSTRACT

An equipment work light ring equipment work light ring includes a light ring and a holding ring. The light ring and the holding ring each include an upper side, a lower side, an inner side, and an outer side. The inner and outer sides of the upper side of the light ring defines therein a circular channel. At a lower portion of the channel are a plurality of angled slots. The lower side of the light ring includes a plurality of apertures defined therein for allowing light to pass therethrough. The outer side of the holding ring includes defined therein a plurality of channels configured for securely engaging and cooperating attaching elements included in the light ring. The equipment work light ring includes a plurality of light emitting diodes for inserting into the angled slots at the lower portion of the channel in the light ring.

16 Claims, 6 Drawing Sheets

EQUIPMENT WORK LIGHT RING

BACKGROUND OF THE INVENTION

1. Field of the Invention

The present invention relates generally to lighting assemblies for machine tools, and more particularly to equipment work light rings.

2. Description of the Related Art

Anyone using machine tool equipment (e.g., horizontal or vertical milling machines, lathes, drill presses, etc.) Knows that one of the most bothersome problems in using the equipment is adequate lighting in the working area of the machine to properly operate the equipment and monitor the process. Most industrial equipment of this type does not have acceptable/usable lighting on the equipment because no conventional work light apparatus or fixture is practical to the task. It is left to the operator to "jury-rig" or find "something" to adequately light the work area environment.

Magnetic or clamp-on lamp assemblies are most often used. These "solutions" all suffer from inadequacies because they are hot, they are high-voltage, they consume large amounts of energy, they are bulky (their housings actually interfere and obstruct the very area needing illumination), they are either fragile or "burn-out" frequently which is expensive, time consuming and inconvenient, they must constantly be re-positioned to light the changing work areas of the machine, they must constantly be re-positioned to different angles, and the like.

Therefore, a need exists for a convenient, inexpensive apparatus to provide even, unobstructive, auxiliary light on machine tools in their work areas.

The related art is represented by the following references of interest.

U.S. Design Pat. Nos. 403,091, 406,370, and 406,669, issued on Dec. 28, 1998, Mar. 2, 1999, and Mar. 9, 1999, respectively, to Gavin McCalla, show ornamental designs for a combination flashlight and powered screwdriver. McCalla '091, '370, and '669 do not suggest an equipment work light ring according to the claimed invention.

U.S. Pat. No. 5,289,355, issued on Feb. 22, 1994 to Benjamin J. Cimock, describes a portable lighted microphone formed in a configuration which outputs light, sound, and color simultaneously. Cimock does not suggest an equipment work light ring according to the claimed invention.

U.S. Pat. No. 5,473,519, issued on Dec. 5, 1995 to John A. McCallops et al., describes a light ring for power tools. McCallops et al. does not suggest an equipment work light ring according to the claimed invention.

U.S. Pat. No. 5,525,842, issued on Jun. 11, 1996 to Jon J. Leininger, describes an air tool with an integrated generator and; a light ring assembly. Leininger does not suggest an equipment work light ring according to the claimed invention.

U.S. Pat. No. 5,615,941, issued on Apr. 1, 1997 to Jules Shecter, describes a an illuminated lollipop holder and storage device. Shecter does not suggest an equipment work light ring according to the claimed invention.

U.S. Pat. No. 5,735,592, issued on Apr. 7, 1998 to Chih-hsien Shu, describes a pen self-illuminating when being used. Shu does not suggest an equipment work light ring according to the claimed invention.

U.S. Pat. No. 5,838,247, issued on Nov. 17, 1998 to Witold S. Bladowski, describes a solid state light system. Bladowski does not suggest an equipment work light ring according to the claimed invention.

U.S. Pat. No. 5,984,493, issued on Nov. 16, 1999 to Frank P. Higgins et al., describes a method and apparatus for selective multi-directional illumination of an object. Higgins et al. does not suggest an equipment work light ring according to the claimed invention.

U.S. Pat. No. 6,030,092, issued on Feb. 29, 2000 to Gavin McCalla et al., describes a lighted handle that can be used to illuminate a tool or work piece secured thereto. McCalla et al. does not suggest an equipment work light ring according to the claimed invention.

U.S. Pat. No. 6,033,081, issued on Mar. 7, 2000 to En Liung Huang, describes a lighted tool. Huang does not suggest an equipment work light ring according to the claimed invention.

U.S. Pat. No. 6,036,087, issued on Mar. 14, 2000 to Yu-Pyo Hong et al., describes a production history information system using a bar code system and a method of the same in which production particulars from a manufacturing process to a sending-out process are entered by using the bar code system and stored by SETs so as to prevent defective products from being sent out and avoid repetitive occurrences of the same failure. Hong et al. does not suggest an equipment work light ring according to the claimed invention.

U.S. Pat. No. 6,168,301 B1, issued on Jan. 2, 2001 to Marvin R. Martinez et al., describes a wheel luminaire. Martinez et al. does not suggest an equipment work light ring according to the claimed invention.

U.S. Pat. No. 6,260,982 B1, issued on Jul. 17, 2001 to John J. Huebner, describes a lighting apparatus capable of by-passing obstructions for illuminating an entire operating machine evenly there across. Huebner does not suggest an equipment work light ring according to the claimed invention.

U.S. Pat. No. 6,318,874 B1, issued on Nov. 20, 2001 to Yutaka Matsunaga, describes power tools having lights that can light a work area. Matsunaga does not suggest an equipment work light ring according to the claimed invention.

U.S. Pat. No. 6,329,676 B1, issued on Dec. 11, 2001 to Toru Takayama et al., describes a flat panel solid state light source. Takayama et al. does not suggest an equipment work light ring according to the claimed invention.

International Patent document WO 01/24583 A1, published on Apr. 5, 2001, describes a light emitting diode (LED) lamp. International '583 does not suggest an equipment work light ring according to the claimed invention.

None of the above inventions and patents, taken either singularly or in combination, is seen to describe the instant invention as claimed.

SUMMARY OF THE INVENTION

The present invention is an equipment work light ring. The equipment work light ring includes a light ring and a holding ring. The light ring includes an upper side and a lower side. The upper and lower sides of the light ring each include inner and outer diameters. The distance from the inner and outer diameters may be dimensioned according to the desires of the user. For example, the outer diameter of the light ring may be four inches, six inches, or the like. An inner side of the light ring integrally interconnects the inner diameters of the upper and lower sides of the light ring. The inner side of the light ring includes a plurality of attaching elements longitudinally extending therefrom. These attaching elements are configured to securely engage and cooperate with channels included within an outer side of the holding ring. An outer side of the light ring integrally interconnects the outer diameters of the upper and lower sides of the light ring.

The inner and outer sides of the upper side of the light ring defines therein a circular channel. At a lower portion of the channel are a plurality of angled slots, such as fifteen degrees, twenty degrees, or the like, that are each configured for positioning therein a light emitting diode (LED). The lower side of the light ring includes a plurality of apertures defined therein for allowing light from LEDs to pass therethrough.

The holding ring magnetically attaches to a housing of a machine tool, such as a milling machine, a lathe, a drill press, or any other machine having a moving/rotating spindle perpendicular to the work. The holding ring is a generally circular element made of durable, rigid material, such as metal, plastic, or the like. The holding ring includes an upper side and a lower side. The upper side includes at least one magnetic element contained therein.

The at least one magnetic element may be a plurality of magnetic elements, such as magnetic disks or the like, distributed about and embedded within the upper side of the holding ring. Alternatively, the at least one magnetic element may by one magnetic ring embedded within the upper side of the holding ring. The upper side of the holding ring may be configured with pockets or a ring channel to contain embedded therein the at least one magnetic element.

The upper and lower sides of the holding ring each include inner and outer diameters. The distance from the inner and outer diameters may be dimensioned according to the desires of the user. An inner side of the holding ring integrally interconnects the inner diameters of the upper and lower sides of the holding ring. An outer side of the holding ring integrally interconnects the outer diameters of the upper and lower sides of the holding ring. The outer side of the holding ring includes defined therein a plurality of channels, such as L-shaped channels or the like, configured for securely engaging and cooperating attaching elements included in the light ring.

The equipment work light ring includes a plurality of LEDs for inserting into the angled slots at the lower portion of the channel in the light ring. The LEDs are preferably low voltage, solid-state, high intensity, white LEDs that are impervious to vibration, shock, impact, or chemicals. Such LEDs have a life expectancy of about 100,000 hours which translates to over eleven years of twenty-four hours a day operation (e.g., virtually infinite with no burn-out replacements required). These LEDs may be electrically interconnected with wiring, as well known in the art.

The equipment work light ring also includes a wiring interconnect for electrically interconnecting the equipment work light ring with an AC adapter, such as a twelve volt AC adapter, for converting utility power to low voltage for the LEDs.

Accordingly, it is a principal aspect of the invention to provide an equipment work light ring including a light ring having an inner side with a plurality of attaching elements extending longitudinally therefrom, a holding ring having at least one magnetic element embedded therein, the holding ring having an outer side with a plurality of channels defined therein and configured to securely engage and cooperate with the attaching elements on the inner side of said light ring, and a plurality of light emitting diodes disposed within the light ring.

It is another aspect of the invention to provide an equipment work light ring including a light ring with an upper side with an inner diameter and an outer diameter, a lower side with an inner diameter and an outer diameter, an inner side and an outer side, wherein the inner side integrally interconnects the inner diameters of the upper side and the lower side of the light ring, and the outer side integrally interconnects the outer diameters of the upper side and the lower side of the light ring.

Still another aspect of the invention is to provide an equipment work light ring including a holding ring having an upper side with an inner diameter and an outer diameter, a lower side with an inner diameter and an outer diameter, and an inner side and an outer side, wherein the inner side integrally interconnects the inner diameters of the upper side and the lower side of the holding ring, and the outer side integrally interconnects the outer diameters of the upper side and the lower side of the holding ring.

It is an aspect of the invention to provide improved elements and arrangements thereof in an equipment work light ring for the purposes described which is inexpensive, dependable and fully effective in accomplishing its intended purposes.

These and other aspects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
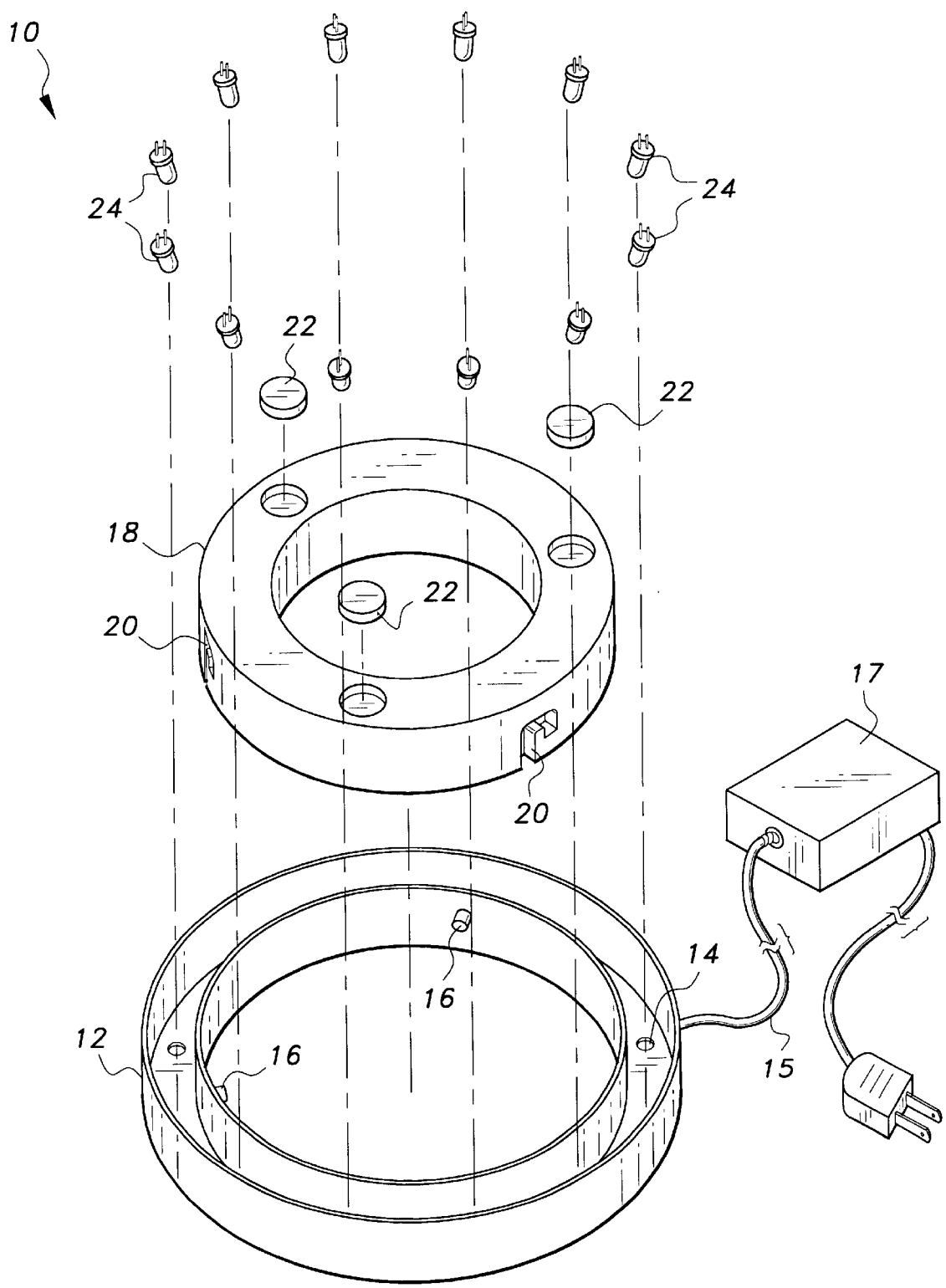
FIG. 1A is an exploded top view of an equipment work light ring according to the present invention.

The present invention is an equipment work light ring. The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

Figure 1B:
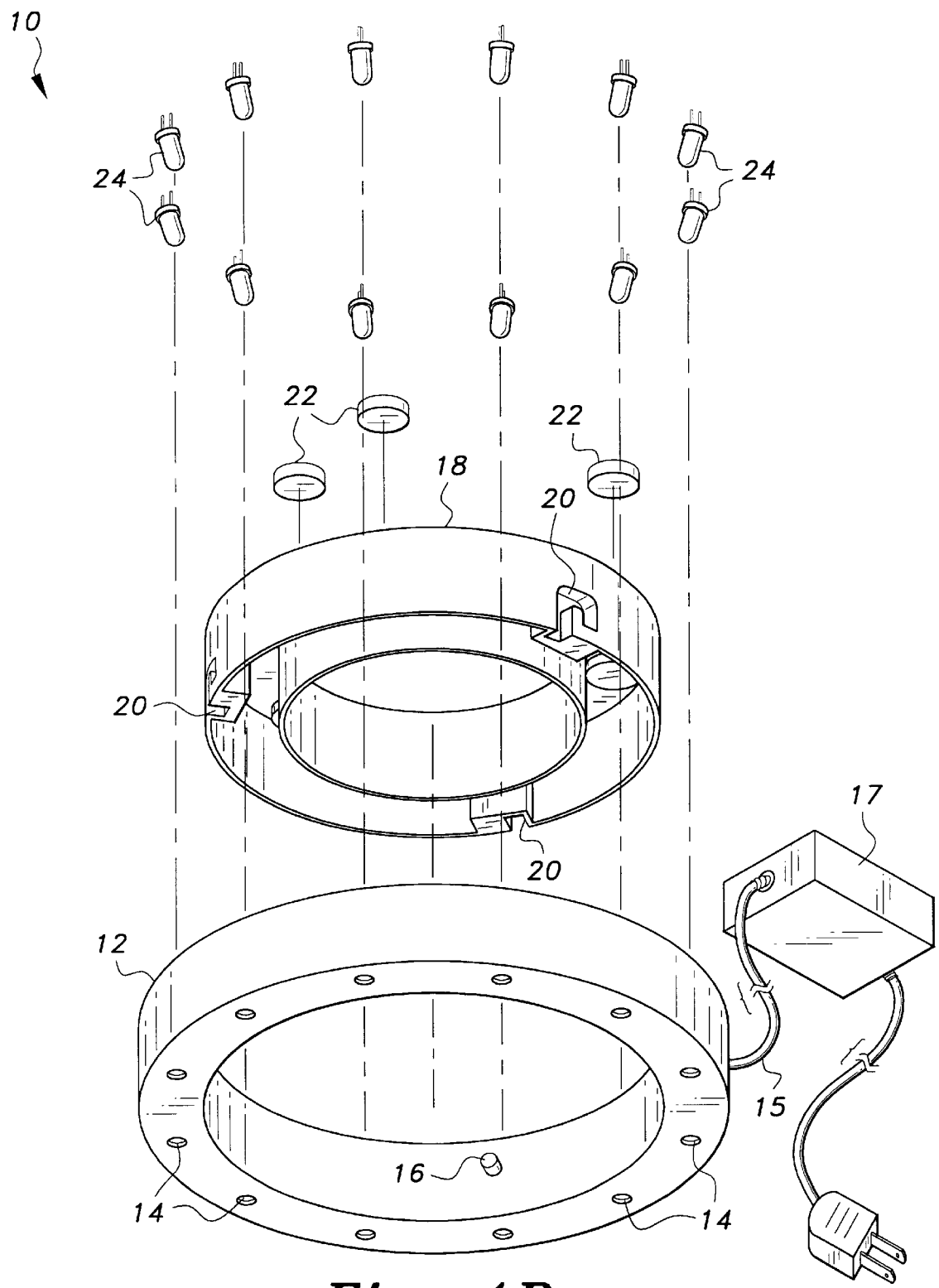
FIG. 1B is an exploded bottom view of the equipment work light ring shown in FIG. 1A.

As shown in the drawings, FIGS. 1A and 1B illustrate one example of an equipment work light ring 10 according to the invention. Equipment work light ring 10 includes a light ring 12 and a holding ring 18.

The light ring 12 includes an upper side and a lower side. The upper and lower sides of the light ring 12 each include inner and outer diameters. The distance from the inner and outer diameters may be dimensioned according to the desires of the user. As illustrated in FIGS. 1A and 1B, the outer diameter of the light ring 12 is dimensioned to be about four inches. An inner side of the light ring 12 integrally interconnects the inner diameters of the upper and lower sides of the light ring 12. The inner side of the light ring 12 includes a plurality of attaching elements 16 longitudinally extending therefrom. These attaching elements 16 are configured to securely engage and cooperate with channels 20 included within an outer side of the holding ring 18.

An outer side of the light ring 12 integrally interconnects the outer diameters of the upper and lower sides of the light ring 12. The inner and outer sides of the upper side of the light ring 12 defines therein a circular channel. At a lower portion of the channel are a plurality of angled slots that are each configured for positioning therein an LED 44. The lower side of the light ring 12 includes a plurality of apertures 14 defined therein for allowing light from LEDs 44 to pass therethrough.

The holding ring 18 magnetically attaches to a housing of a machine tool, such as a milling machine, a lathe, a drill press, or any other machine having a moving/rotating spindle perpendicular to the work. The holding ring 18 is a generally circular element made of durable, rigid material, such as metal, plastic, or the like. The holding ring 18 includes an upper side and a lower side. The upper side includes at least one magnetic element contained therein.

The at least one magnetic element may be a plurality of magnetic elements, such as magnetic disks or the like, distributed about and embedded within the upper side of the holding ring 18. Alternatively, the at least one magnetic element may by one magnetic ring embedded within the upper side of the holding ring. As shown in FIGS. 1A and 1B, the holding element includes three magnetic disks 22.

The upper side of the holding ring may be configured with pockets or a ring channel to contain embedded therein the at least one magnetic element. The upper and lower sides of the holding ring 18 each include inner and outer diameters. The distance from the inner and outer diameters may be dimensioned according to the desires of the user. An inner side of the holding ring integrally interconnects the inner diameters of the upper and lower sides of the holding ring. An outer side of the holding ring 18 integrally interconnects the outer diameters of the upper and lower sides of the holding ring 18. The outer side of the holding ring includes defined therein a plurality of channels 20, such as L-shaped channels or the like, configured for securely engaging and cooperating attaching elements 16 included in the light ring 12.

The equipment work light ring includes a plurality of LEDs 24 for inserting into the angled slots at the lower portion of the channel in the light ring 12. The LEDs 24 are preferably low voltage, solid-state, high intensity, white LEDs that are impervious to vibration, shock, impact, or chemicals. Such LEDs 24 have a life expectancy of about 100,000 hours which translates to over eleven years of twenty-four hours a day operation (e.g., virtually infinite with no burn-out replacements required). These LEDs 24 may be electrically interconnected with wiring, as well known in the art.

The equipment work light ring 10 also includes a wiring interconnect 12 for electrically interconnecting the equipment work light ring with an AC adapter 17, such as a twelve volt AC adapter, for converting utility power to low voltage for the LEDs 24.

Figure 2A:
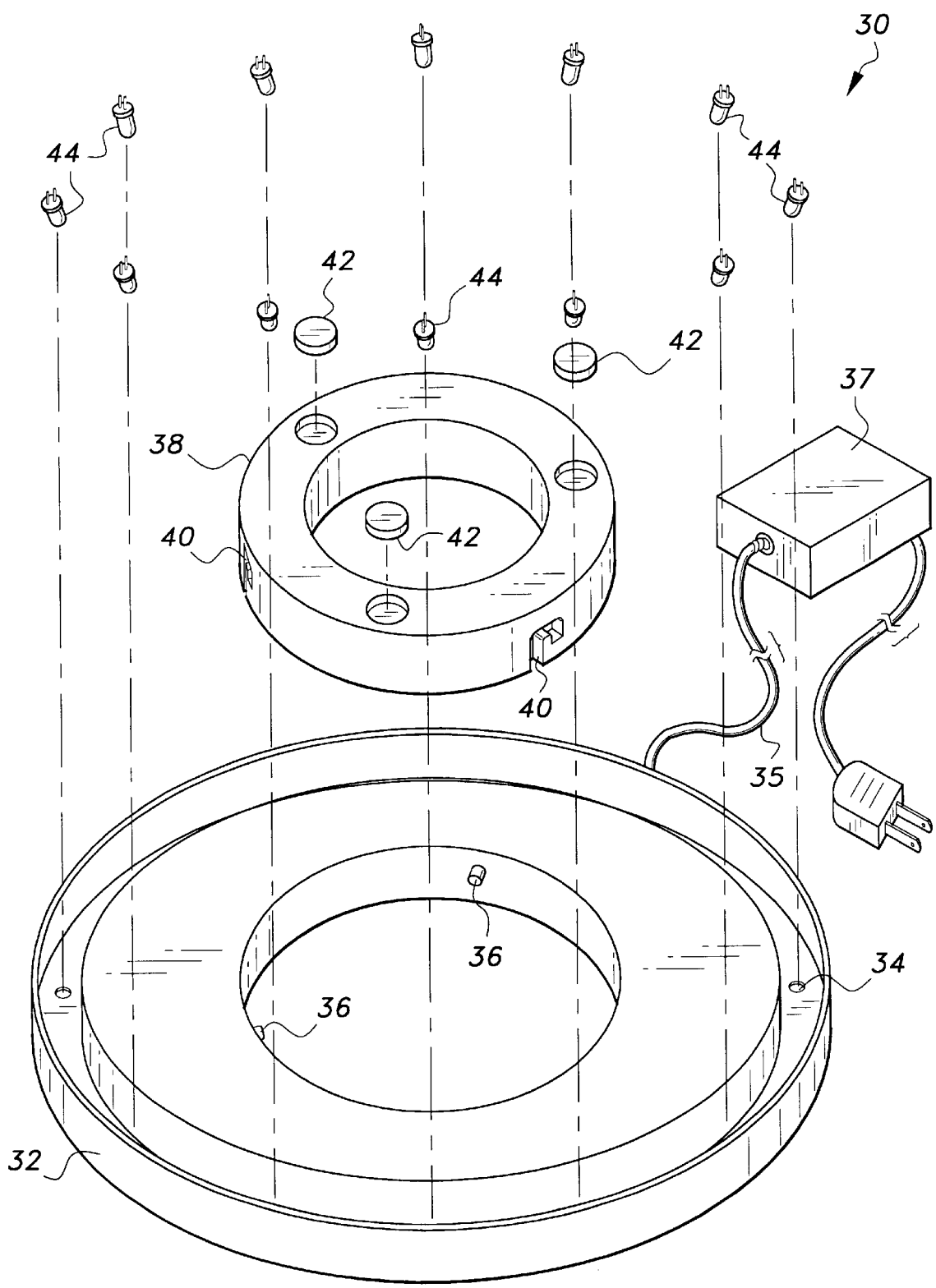
FIG. 2A is an exploded top view of an equipment work light ring according to the present invention.
Figure 2B:
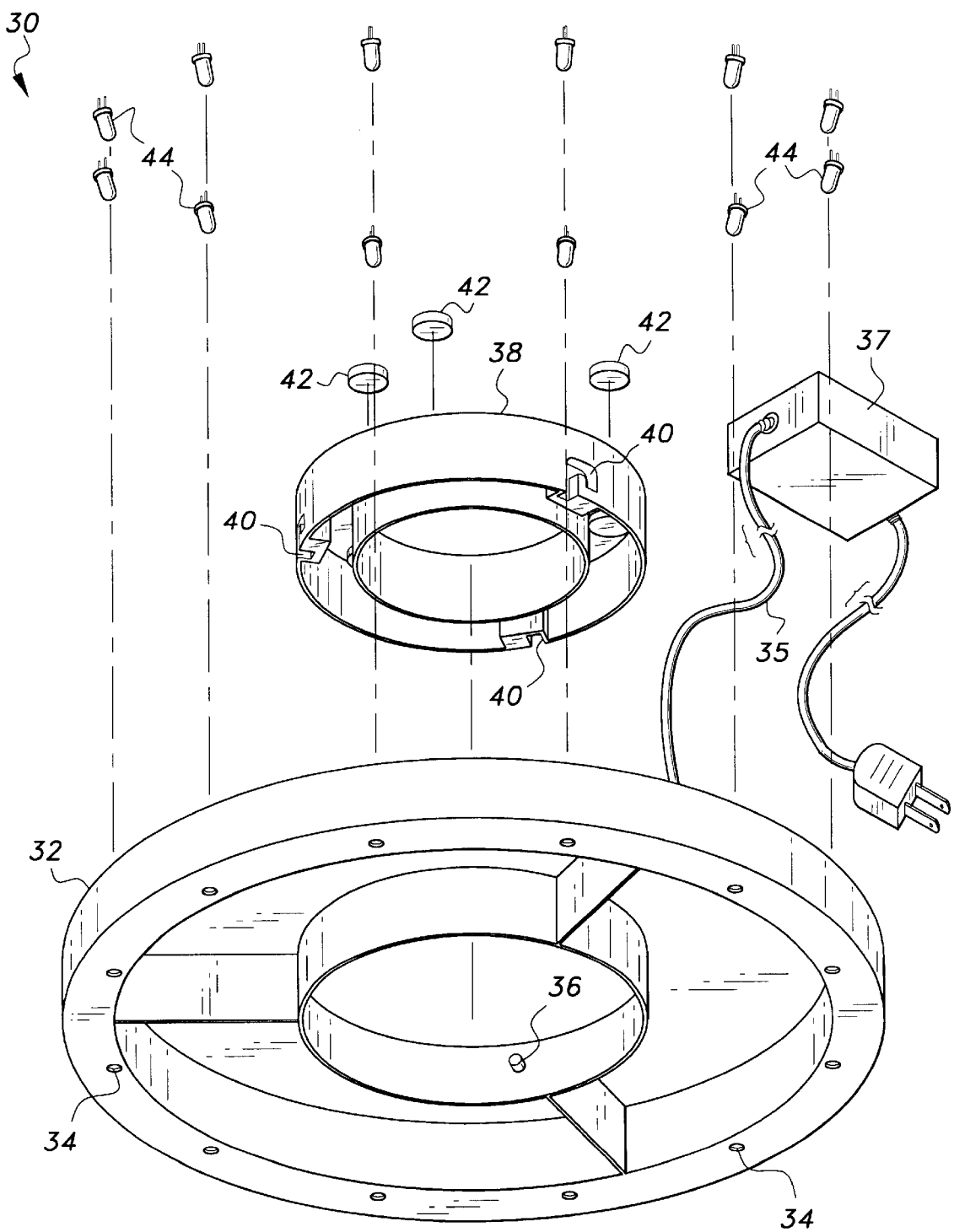
FIG. 2B is an exploded bottom view of the equipment work light ring shown in FIG. 2A.

FIGS. 2A and 2B illustrate another example of an equipment work light ring 30 according to the invention. Equipment work light ring 30 includes a light ring 32 and a holding ring 38.

The light ring 32 includes an upper side and a lower side. The upper and lower sides of the light ring 32 each include inner and outer diameters. The distance from the inner and outer diameters may be dimensioned according to the desires of the user. In this example, the outer diameter of the light ring 32 is about six inches. An inner side of the light ring 32 integrally interconnects the inner diameters of the upper and lower sides of the light ring 32. The inner side of the light ring 32 includes a plurality of attaching elements 36 longitudinally extending therefrom. These attaching elements 36 are configured to securely engage and cooperate with channels 40 included within an outer side of the holding ring 38.

An outer side of the light ring 32 integrally interconnects the outer diameters of the upper and lower sides of the light ring 32. The inner and outer sides of the upper side of the light ring 32 defines therein a circular channel. At a lower portion of the channel are a plurality of angled slots that are each configured for positioning therein an LED 44. The lower side of the light ring 32 includes a plurality of apertures 34 defined therein for allowing light from LEDs to pass therethrough.

The holding ring 38 magnetically attaches to a housing of a machine tool, such as a milling machine, a lathe, a drill press, or any other machine having a moving/rotating spindle perpendicular to the work. The holding ring 38 is a generally circular element made of durable, rigid material, such as metal, plastic, or the like. The holding ring 38 includes an upper side and a lower side. The upper side includes at least one magnetic element contained therein. The at least one magnetic element may be a plurality of magnetic elements, such as magnetic disks or the like, distributed about and embedded within the upper side of the holding ring 38. Alternatively, the at least one magnetic element may by one magnetic ring embedded within the upper side of the holding ring. As shown in FIGS. 2A and 2B, the holding element includes three magnetic disks 42.

The upper side of the holding ring 38 may be configured with pockets or a ring channel to contain embedded therein the at least one magnetic element. The upper and lower sides of the holding ring 38 each include inner and outer diameters. The distance from the inner and outer diameters may be dimensioned according to the desires of the user. An inner side of the holding ring integrally interconnects the inner diameters of the upper and lower sides of the holding ring. An outer side of the holding ring 38 integrally interconnects the outer diameters of the upper and lower sides of the holding ring. The outer side of the holding ring 38 includes defined therein a plurality of channels 40, such as L-shaped channels or the like, configured for securely engaging and cooperating attaching elements included in the light ring.

The equipment work light ring 30 includes a plurality of LEDs 44 for inserting into the angled slots at the lower portion of the channel in the light ring 32. The LEDs 44 are preferably low voltage, solid-state, high intensity, white LEDs that are impervious to vibration, shock, impact, or chemicals. Such LEDs 44 have a life expectancy of about 100,000 hours which translates to over eleven years of twenty-four hours a day operation (e.g., virtually infinite with no burn-out replacements required). These LEDs 44 may be electrically interconnected with wiring, as well known in the art.

The equipment work light ring also includes a wiring interconnect 35 for electrically interconnecting the equipment work light ring with an AC adapter 37, such as a twelve volt AC adapter, for converting utility power to low voltage for the LEDs 44.

Figure 3A:
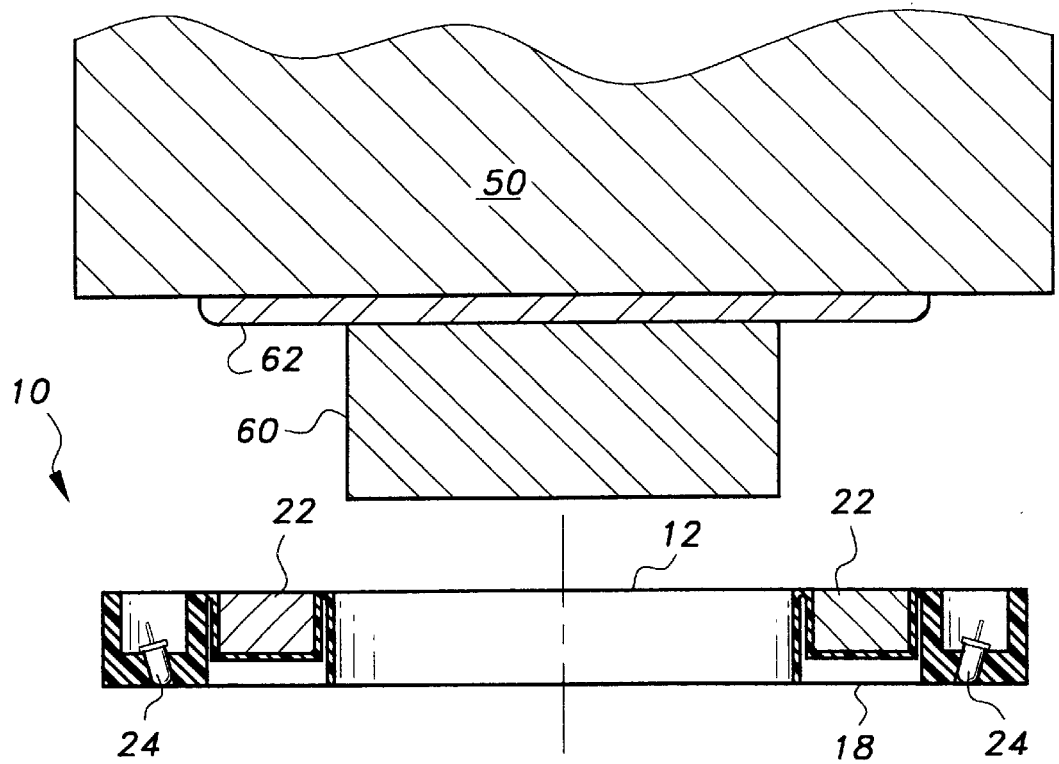
FIG. 3A is a cross-sectional diagram of the equipment work light ring shown in FIGS. 1A and 1B separated from a work tool (vertical mill nose).
Figure 3B:
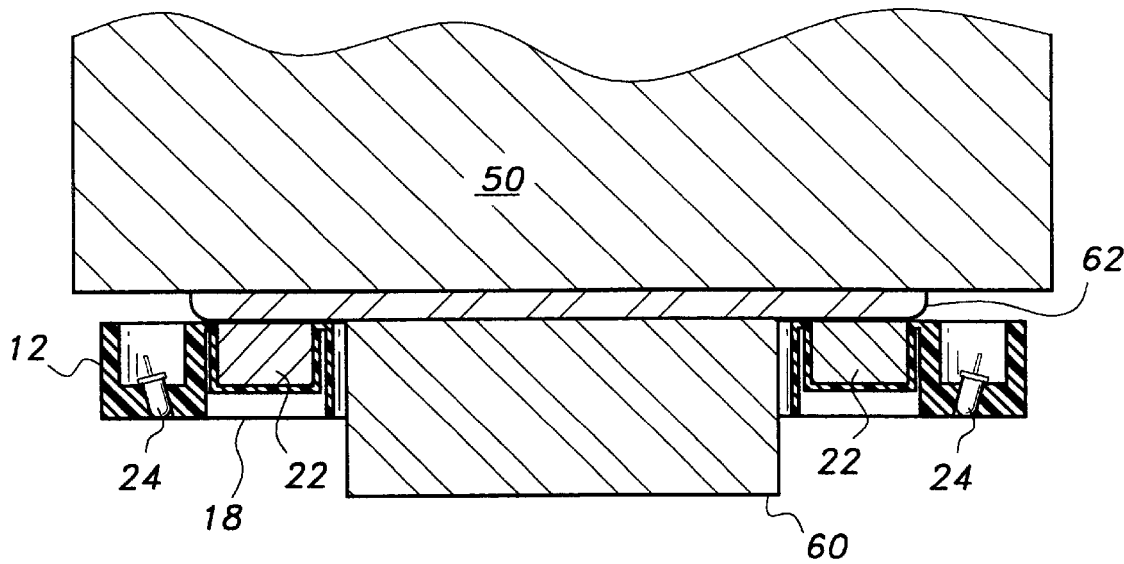
FIG. 3B is a cross-sectional diagram of the equipment work light ring shown in FIGS. 1A and 1B connected to a retractable spindle.
Figure 3C:
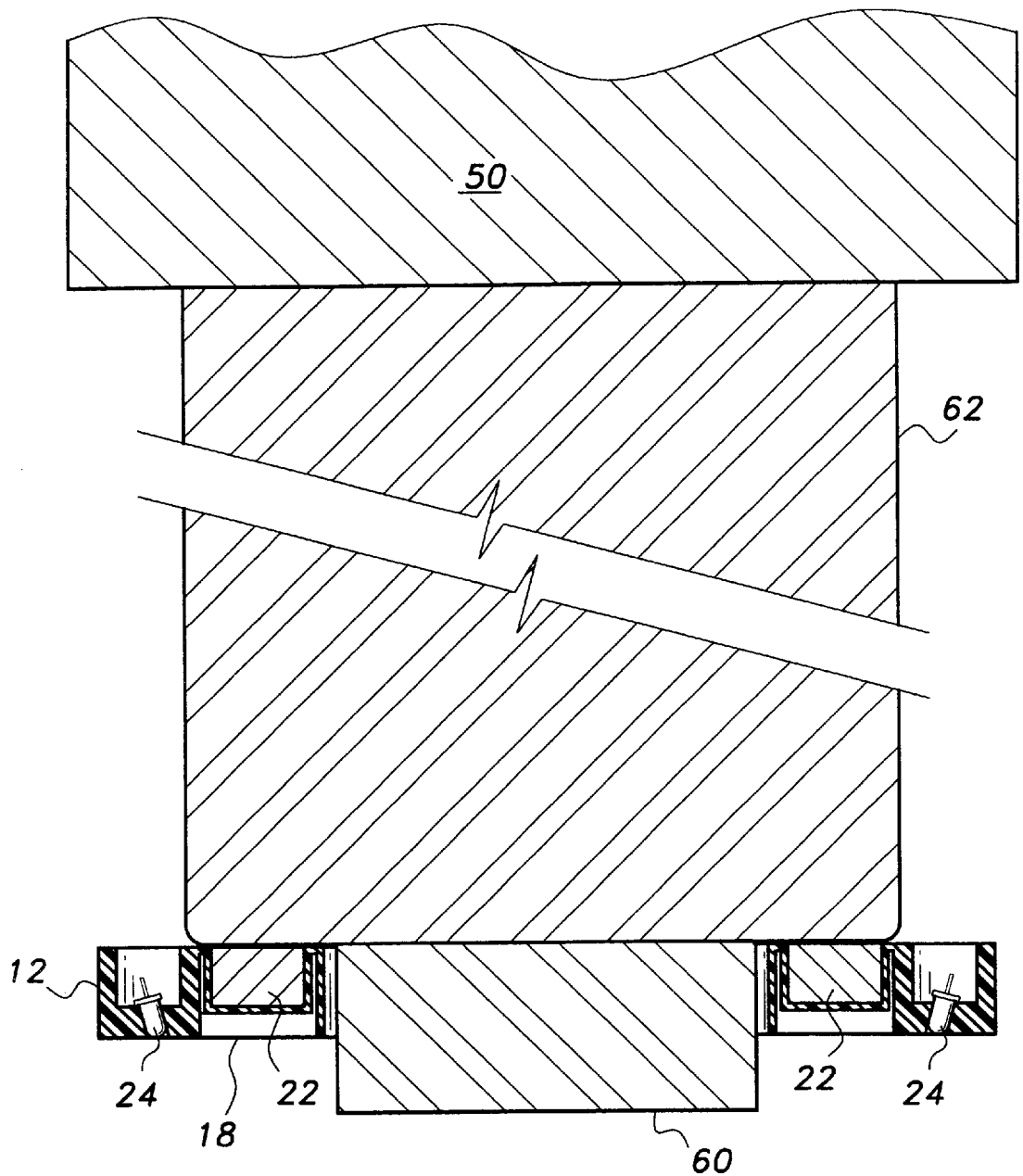
FIG. 3C is a cross-sectional diagram of the equipment work light ring shown in FIGS. 1A and 1B connected to an extended spindle.

FIG. 3A illustrates a cross-sectional diagram of the equipment work light ring 10 shown in FIGS. 1A and 1B separated from a work tool (vertical mill stand). The vertical mill nose 50 includes a rotating spindle 60 and a movable spindle housing 62. The equipment work light ring 10 includes embedded magnet elements 22 and LEDs 24 inserted into angled slots. FIG. 3B illustrates the equipment work light ring magnetically attached to movable spindle housing 62. FIG. 3C illustrates the equipment work light ring magnetically attached to the extended movable spindle housing 62.

The equipment work light rings 10,30 provide 360° of even, high intensity, focused, non-directional lighting of the work area. As such, any angle of view of the work area or tooling is seen uniformly and is unimpeded by the equipment work light rings 10,30. This 360° illumination eliminates false relative views and shadowing of tooling and work material so prevalent when, directional lighting is used. Because the equipment work light rings 10,30 may be magnetically attached to spindle housings, they follow the machine tooling as it performs its operations. Unlike any other form of auxiliary lighting, the equipment work light rings 10,30 are not attached to a machine frame. This aspect of the invention continues to provide illumination in the actual working area and will not change the relative position of the light output at the tooling work area as work is positioned or progresses.

The equipment work light rings 10,30 operate at low voltages (e.g., twelve volts or the like) which eliminates a very real shock hazard present with current auxiliary light fixtures in a wet, caustic, abrasive, metal contaminated environment. The LEDs 22,42 of the equipment work light rings 10,30 produce no heat which eliminates a very real burn hazard. The camlock feature of the light rings 12,32 allow for rapid change out to larger diameter light rings, without having to first remove tooling, when larger tooling is required on a machine tool.

The equipment work light ring configuration is easily used, or transferred to, any milling machine, lathe tail stock, drill press, or any other machine having a moving/rotating spindle perpendicular to the work. The equipment work light ring consumes only about eighty milliamps (one watt) of power compared to a typical 40 or 60 watt light bulb. Due to the magnet elements of the holding rings, there is no drilling, screwing, glueing, or any other special method of attachment required. Once attached, the equipment work light ring 10,30 can stay on the machine tool and does not interfere in any way with the action of the machine tool, the operator, or the view of the machine work area. In addition, if desired, it is very easy to "pop" a equipment work light ring off a machine tool and transfer the equipment work light ring to another machine tool without any tools needed.

Different sizes (diameters) of light rings are quickly changeable depending upon requirements. For example, a four inch light ring may be used for standard mill or lathe tooling due to its small size which does not interfere with viewing the work area yet provides properly focused light in those tight areas. A six inch light ring may be used for large chucks or other large tooling providing properly focused 360° around the tooling and onto the work surface/area. The inner diameter of these multiple sizes of light rings make them changeable without having to first remove tooling.

While the invention has been described with references to its preferred embodiment, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teachings.

I claim:

1. An equipment work light ring comprising:
   a light ring having an inner side with a plurality attaching elements extending longitudinally therefrom;
   a holding ring having at least one magnetic element embedded therein, said holding ring having an outer side with a plurality of channels defined therein and configured to securely engage and cooperate with the attaching elements on the inner side of said light ring; and
   a plurality of light emitting diodes disposed within said light ring.

2. The equipment work light ring according to claim 1, wherein said light ring further comprises an upper side with an inner diameter and an outer diameter, a lower side with an inner diameter and an outer diameter, and an outer side, wherein the inner side integrally interconnects the inner diameters of the upper side and the lower side of said light ring, and the outer side integrally interconnects the outer diameters of the upper side and the lower side of said light ring.

3. The equipment work light ring according to claim 2, wherein said outer diameters of said upper and lower sides are about four inches.

4. The equipment work light ring according to claim 2, wherein said outer diameters of said upper and lower sides are about six inches.

5. The equipment work light ring according to claim 2, wherein the upper side of said light ring has defined therein a generally circular channel with a lower portion.

6. The equipment work light ring according to claim 5, wherein said lower portion of the channel has defined therein a plurality of angled slots each configured to receive a light emitting diode.

7. The equipment work light ring according to claim 6, wherein said angled slots are angled at about fifteen degrees.

8. The equipment work light ring according to claim 6, wherein said angled slots are angled at about twenty degrees.

9. The equipment work light ring according to claim 2, wherein said lower side of said light ring has defined therein a plurality of apertures to allow light to pass therethrough.

10. The equipment work light ring according to claim 1, wherein said holding ring further comprises an upper side with an inner diameter and an outer diameter, a lower side with an inner diameter and an outer diameter, and an outer side, wherein the inner side integrally interconnects the inner diameters of the upper side and the lower side of said holding ring, and the outer side integrally interconnects the outer diameters of the upper side and the lower side of said holding ring.

11. The equipment work light ring according to claim 10, wherein said upper side of said at least one magnetic element is a plurality of magnetic disks.

12. The equipment work light ring according to claim 10, wherein said upper side of said at least one magnetic element is a magnetic ring.

13. The equipment work light ring according to claim 1, wherein said plurality of channels are L-shaped channels.

14. The equipment work light ring according to claim 1, wherein said plurality of light emitting diodes are low voltage, solid-state, high intensity, white light emitting diodes.

15. The equipment work light ring according to claim 1, further comprising a wiring interconnect for electrically interconnecting said equipment work light ring with an external power source.

16. The equipment work light ring according to claim 1, wherein said external power source is utility power.

* * * * *